United States Patent [19]

Neiner et al.

[11] Patent Number: 5,161,971
[45] Date of Patent: Nov. 10, 1992

[54] DENTAL INSTRUMENT

[75] Inventors: Karen L. Neiner, Chicago; Roy E. Riihimaki, Libertyville, both of Ill.; Sharon Burns, Mission Hills, Kans.

[73] Assignee: Hu-Friedy Mfg. Co., Inc., Chicago, Ill.

[21] Appl. No.: 691,126

[22] Filed: Apr. 25, 1991

[51] Int. Cl.⁵ .............................. A61C 3/00
[52] U.S. Cl. ................... 433/141; 401/195
[58] Field of Search ............ 433/141, 142, 143, 144, 433/145, 146, 147, 70, 68, 75; 132/308, 309, 310, 311, 321, 328, 329; 401/195

[56] References Cited

U.S. PATENT DOCUMENTS

| | | | |
|---|---|---|---|
| 90,235 | 5/1869 | Burrows | 132/311 |
| 97,391 | 11/1869 | Graham et al. | 132/328 |
| D. 310,308 | 9/1990 | Wolsey | 401/195 |
| 2,199,922 | 5/1940 | McManis et al. | 132/308 |
| 4,768,531 | 9/1988 | Broussard | 401/195 |

Primary Examiner—Cary E. O'Connor
Attorney, Agent, or Firm—Dressler, Goldsmith, Shore, Sutker & Milnamow, Ltd.

[57] ABSTRACT

An autoclavable instrument for use in discovering and recording information during a dental examination includes a handpiece with a dental probe at one end and a pen at the other. The pen may be reversed or otherwise sealed to withstand autoclaving.

7 Claims, 2 Drawing Sheets

DENTAL INSTRUMENT

FIELD OF INVENTION

This invention relates to a probe for use in dental examinations and diagnosis More particularly, it relates to a pen-probe for use in discovering and recording information during a periodontal examination, which is also able to withstand sterilization procedures.

Routine dental examinations are a very important and integral component in the practice of dentistry. During these examinations, anything from cavities and simple gingivitis to advanced periodontitis may be discovered. During all these procedures, however, any information which is discovered by the dentist or hygienist must be documented for each patient.

Currently, when dentists and hygienists examine a patient using special dental probes, they intermittently record the relevant information on periodontal charts. These probing procedures help the dentist discover a variety of information, including gum tissue health, spacings between the teeth and gums, and the existence of periodontal diseases. Unfortunately, the methods used today by dentists and hygienists to record such information are inherently problematic in relation to sterilization and efficiency. Typically, the dentist will first probe the teeth and then record the disposition information on the periodontal chart. To do this, the dentist must sequentially probe the tooth, put the probe down, pick up the pen, record the information, put the pen down, pick the probe up again, and then repeat the entire process. This method, in addition to being bothersome and tedious, is an unsterile and inefficient means of practicing dentistry.

When a patient is examined, each instrument is sterilized before the procedure so as to protect the patient and clinician from the spread of disease. In addition to the sterilized instruments, most dental workers also use masks and surgical gloves for protection. The pen with which relevant information is recorded, however, stays either in the clinician's pocket, on operatory counter top, or is transferred from one patient's instrument tray to another, and is not sterilized. Indeed, a standard ball-point or other type of pen cannot be sterilized due to the heat, pressure and moisture of an autoclave. This transferring of the pen from patient to patient, coupled with the repeated picking up, recording, and putting down procedure, greatly increases the chances for spreading disease.

When performing dental examinations, the clinician's fingers are alternately exposed to the patient's mouth and used to grasp the pen and record information on the periodontal chart. As a result, the pen becomes coated with many microbes from the patient's mouth. When the next patient is examined, the clinician has washed, changed gloves and masks, and has a newly sterilized set of instruments, but the same unsterilized pen is used. The germs from the first patient are thus transferred to the second patient, and additional microbes from the second patient are also transferred onto the pen. Upon the arrival of additional patients, germs from the first and second patient may be transferred to the new patients, fresh microbes are gathered from these patients, and the cycle continues. Without sterilizing the pen, therefore, many different people are exposed to a number of diseases. In view of the current acquired immunodeficiency syndrome (AIDS) epidemic, moreover, sterilization of equipment has become a matter of even higher priority.

In addition, the current methods used by dentists are inefficient. For example, the normal adult mouth has thirty-two teeth, and each tooth requires six measurements. Therefore, a dentist will make a total of 192 measurements on one patient's mouth, all which must be recorded, taking up a considerable amount of time. Most routine dental appointments last thirty to sixty minutes and include (in addition to charting a patient's mouth) x-rays, teeth cleanings, and consultations with the dentist. Currently, using the pick up, record, put down, pick up, and repeat method, a full charting of a patient's mouth takes roughly twenty minutes. This is a large portion of the entire appointment time. If the pen and probe did not have to be continuously switched, the time consumed could be significantly reduced, or more time could be devoted to the examination.

A final problem also arises in relation to the alternate use of probe and pen. Even though a dentist or hygienist may be very careful, there is a greater risk that instruments will be dropped and thus contaminated or possibly even damaged when they are continually picked up and put down. Even if the damage does not render the instruments useless, any resulting scratches may make the instruments more vulnerable to contamination problems. Furthermore, if an instrument is damaged or contaminated during an examination, it will require replacement before the procedure continues. This replacement time again leads to further inefficiency in the examination process.

SUMMARY OF INVENTION

Accordingly, it is an object of the present invention to provide a dental pen-probe which may be used by dental personnel during examinations for both discovering and recording information concerning a patient's teeth and surrounding supporting tissues, and which is able to withstand sterilization procedures.

It is another object of the present invention to provide a dental pen-probe which is equipped with a reversible ball-point pen.

It is another object of the present invention to provide a dental pen-probe which allows a dentist both to examine patients and record information more accurately and efficiently.

It is another object of the present invention to provide a dental pen-probe which decreases the risk of transfer of germs and disease from one dental patient to another or from patient to clinician.

It is another object of the present invention to provide a dental pen-probe which increases efficiency in the practice of dentistry.

In accordance with these objectives, the present invention provides a sterilizable dental instrument comprising a handpiece, a dental probe at one end of the handpiece, and writing means at the other end thereof. The handpiece is preferably constructed from an autoclavable material and has means including a cavity for receiving and sealing the writing means within the cavity during autoclaving of the instrument. In a preferred embodiment the sealing means comprises a threaded connection to the instrument. The writing means must be able to withstand autoclaving temperature, and may comprise a writing point and a reservoir containing a non-labile ink. It is also contemplated that the instrument may have means for reversibly mounting the writing means in the cavity with the writing point alternately protruding from, or sealed within, the cavity, depending on whether the instrument is in use or is being autoclaved.

The writing means is preferably a ball-point pen employing a pressurized Fisher Space Pen ink cartridge which is able to withstand sterilization temperatures and pressures.

When using the invention, a dentist or hygienist takes a newly sterilized pen-probe from its sterilization tray and unscrews the pen portion, thus exposing the ball-point pen and its threaded end. The pen is then reversed and its opposite end is screwed into the threaded cavity of the handpiece. The clinician then examines the patient with the probe end of the instrument, taking measurements of the teeth for recordation purposes. After each series of measurements, the clinician simply pivots the pen-probe in hand, records the information on the periodontal chart with the pen end, and then pivots the pen-probe again to resume work on the patient's mouth. The instrument never leaves the clinician's hand, and thus the risk of damage and/or contamination from inadvertently dropping it is greatly reduced.

After the dentist o hygienist finishes the examination process, the pen portion is again unscrewed, reversed and rescrewed into the threaded cavity of the handpiece, making sure that the threaded pen portion is now tightly sealed within the cavity. The pen-probe may then be sterilized in an autoclave or similar apparatus. With the pen point sealed in the cavity, there is no risk of ink bleeding and spreading onto the other instruments in the autoclave. Furthermore, despite the heat and pressure of the autoclave, the ink from the pen Fisher Space Pen ball-point cartridge will not leak or bleed inside the cavity because of its pressure- and heat-resistant qualities. Once the pen-probe is sterilized, the dentist or hygienist may re-use it on the next patient without any risk of contagion.

These and other features, objects and advantages of the invention will become apparent from the following detailed description of an illustrative embodiment of the invention, in which reference is made to the accompanying drawings.

DETAILED DESCRIPTION OF THE INVENTION

Figure 2:
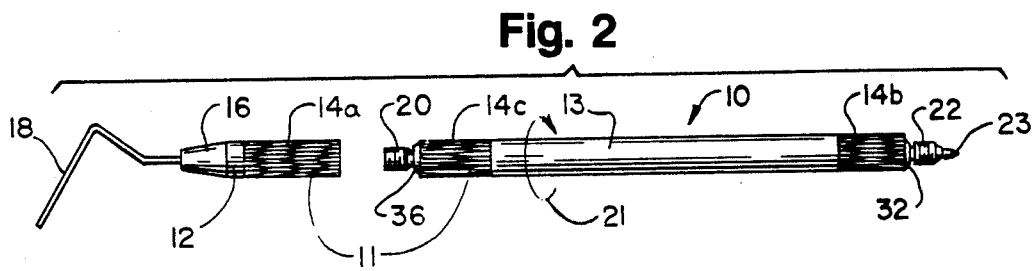
FIG. 2 is a similar view of the same instrument, but with the pen-probe separated into its two component pieces with the opposite end ready to screw into the threaded cavity.
Figures 3, 4:
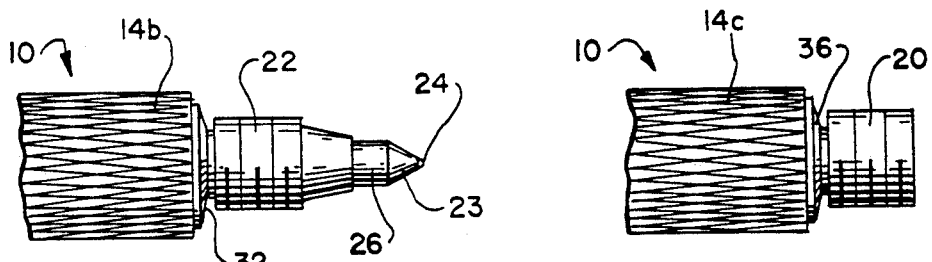
FIG. 3 is a fragmentary elevation of the ball-point pen end of the same instrument.
FIG. 4 is a fragmentary elevation of the same instrument, depicting the opposite end of the pen portion.
Figure 5:
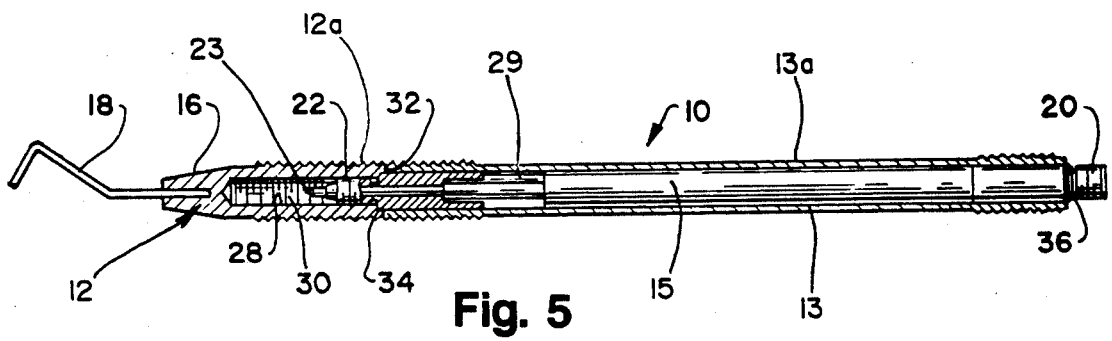
FIG. 5 is an enlarged cross-section of the same instrument, depicting the writing end of the ball-point pen portion screwed into the threaded cavity.

In accordance with this invention, a dental instrument generally designated 10 is provided to allow dental personnel to both discover and record information during a dental examination, and then subsequently sterilize said instrument safely and effectively. The instrument 10 is a pen-probe combination which comprises a cylindrical handpiece 11 which separates (as seen in FIG. 2) into a probe portion 12 and a pen portion 13 by means of a threaded connection to be described. The probe portion 12 has a gripping section 14a with a knurled exterior, and an interior cavity 28 (see FIG. 5) formed with internal threads 30 and a conically beveled entrance 34. The probe portion 12 tapers to a conical end 16 and has a conventional periodontal probe 18 extending from said end. The pen portion 13 has knurled gripping sections 14b, 14c at each end, and an internal cavity 29 (see FIG. 5) which encases a sealed pressurized ball-point ink cartridge 15. This cartridge extends outwardly from one end of the pen portion 13 and terminates in a ball-point pen tip 23 which is held in place by an externally threaded sleeve 22 with a beveled shoulder 32 secured to the pen portion 13. An externally threaded plug 28, which also has a beveled shoulder 36, extends from the other end of the pen portion 13. Either the threaded plug 20 or the threaded sleeve 22 can mate with the internal threads 30 of the probe portion 12 (FIG. 5).

Figure 6:
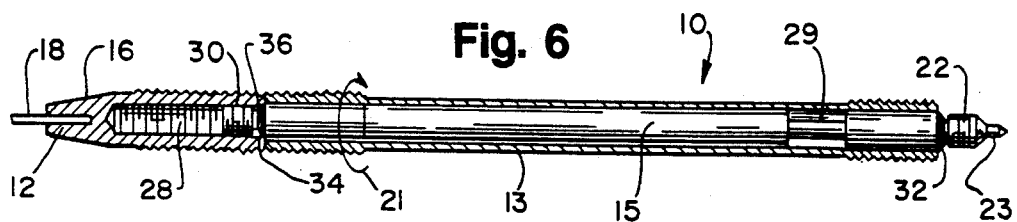
FIG. 6 is a similar enlarged cross-section of the same instrument, depicting the opposite end of the pen portion screwed into the threaded cavity.
Figure 7:
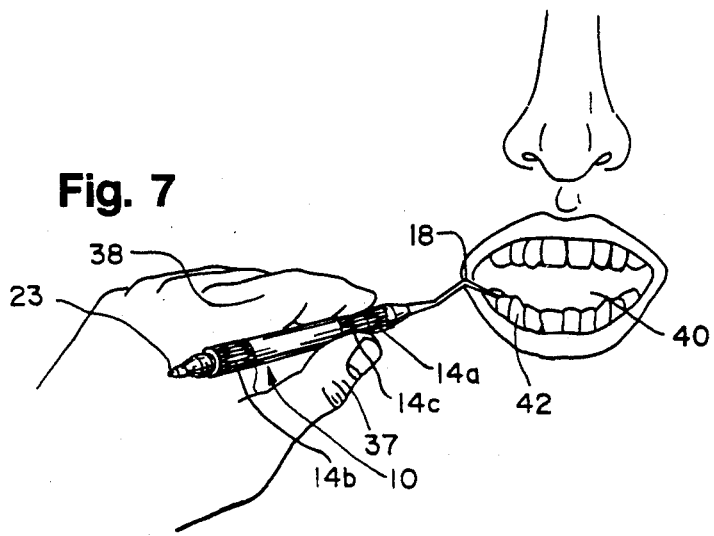
FIG. 7 is a perspective view of the same instrument, depicting a dentist or hygienist using it to examine a patient's mouth.
Figure 8:
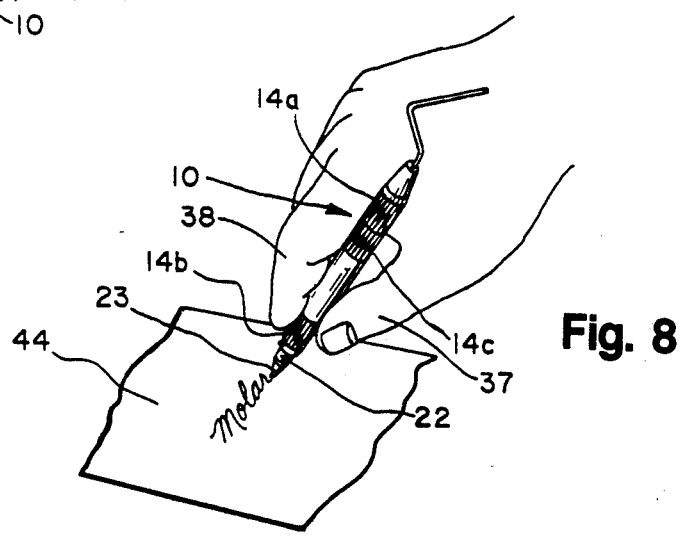
FIG. 8 is a similar perspective view of the same instrument, depicting the dentist or hygienist using it to record relevant information on a chart during the examination.

When the threaded sleeve 22 on the pen end of the portion 13 mates with the internal threads 30 (as illustrated in FIGS. 2 and then the exposed ball-point pen tip 23 is protected within the cavity 28, and a tight seal is afforded by the engagement of conically bevelled surfaces 34 and 32. This is the autoclavable configuration of the pen-probe 10. On the other hand, when the threaded plug 20 on the opposite end of the portion 13 mates with the internal threads 30 (as illustrated in FIGS. 6, 7 and 8), then the conically beveled surface 36 engages the conically bevelled surface 34, and the pen point 23 is at the distal end of the instrument 10 in position for recording notes relating to a periodontal examination.

The external casings 11a and 13a (see FIG. 5) of the probe portion 12 and pen portion 13 respectively are constructed out of chrome-plated brass or a similar heat-resistant material which may be sterilized in an autoclave so that the pen-probe 10 may be safely re-used. The threaded plug 20 and the threaded sleeve 22, as well as the probe 18 extending from the conical end 16 of the first piece 12, are also constructed out of stainless steel or similar heat-resistant material to withstand the autoclave environment.

The encased ink cartridge 15 and ball-point pen point 23 are preferably the Fisher Space Pen brand, manufactured by the Fisher Pen Company of Forest Park, IL, which employs a sealed-pressurized ink cartridge (U.S. Pat. No. 3,425,779) to hold the ink, and an ultra-hard tungsten carbide ball 24 and stainless steel, precision-machined socket 26, to insure smooth writing and no leakage of ink. Tests have shown that this type of ball-point pen assembly is capable of withstanding the heat and pressure of an autoclave without impairing its operation as a writing instrument. Furthermore, the Fisher Space Pen is the only known type of ink cartridge which will not explode in the autoclave and cause damage. It is necessary, however, that the pen be protected from the steam of the autoclave by means of the sealed cavity 28, otherwise the ink will escape into the autoclave and leave inkstains inside the autoclave and on its contents.

Figure 9:
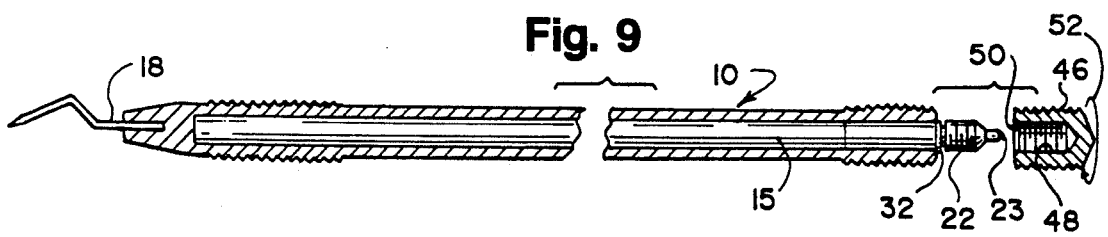
FIG. 9 is a fragmentary cross-section of an alternative embodiment of the invention, employing a threaded overcap.

In an alternative embodiment of the invention, as seen as FIG. 9, the encased ink cartridge 15 is permanently fixed within the instrument 10 at the end opposite the periodontal probe 18. In this embodiment, the pen is not reversible and is always exposed. Therefore, in order to seal the ball-point pen point 23 from the steam of the autoclave, an overcap 46 with internal threads 48 and a conically beveled surface 50 is provided.

Figure 1:
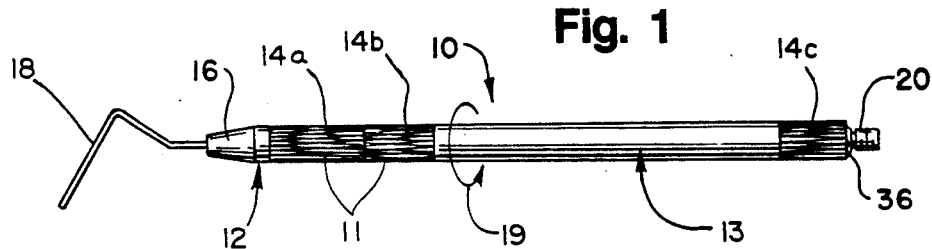
FIG. 1 is an exploded elevation of a preferred embodiment of a pen-probe in accordance with the invention, depicted in assembled condition with the ball-point pen end enclosed in the threaded cavity.

The operation of the invention will now be described. As seen in FIG. 1, the pen-probe 10 is taken from the autoclave (not shown) with the pen tip 23 enclosed in the protective cavity 28. The threaded connection 22–30 is then unscrewed as illustrated by arrow 19, thus separating the pen-probe into its two portions 12 and 13. The pen portion 13 is then reversed to the position shown in FIG. 2, and the threaded plug 20 is subsequently screwed into the cavity 28 of the probe portion 12, as illustrated by arrow 21 in FIGS. 2 and 6. This allows both the pen point 23 and the periodontal probe 18 to be utilized during an examination. When the plug 20 is tightly threaded into the cavity 28 as seen in FIG. 6, the beveled shoulder 36 of the plug snugly fits against the beveled opening 34 of the cavity, thus firmly securing the instrument 10 into a single unit for use during examination and writing.

Once the pen point 23 is thus exposed and the threaded connection 22–30 secured, the instrument 10 may be held by the thumb 37 and forefinger 38 at the knurled gripping sections 14a, 14c, which have now merged into one gripping section at the connection between the probe portion 12 and the pen portion 13.

(As seen in FIGS. 1, 7 and 8, however, the pen-probe 10 is designed so that either gripping section 14b or 14c of the pen portion 13 will match up with the gripping section 14a of the probe portion 12, and therefore allow a dentist to achieve maximum control and dexterity even when examining a patient, whether the pen is exposed or not).

As shown in FIG. 7, the dentist then proceeds to direct the probe 18 into the patient's mouth 40 and begins examining the patient to collect information concerning the patient's teeth and gums 42. Once the information is collected, the dentist removes the instrument 10 from the patient's mouth 40, reverses the pen-probe 10 to the position of FIG. 8, holds the instrument by the knurled gripping section 14b, and uses the pen point 23 to record the information on the patient's periodontal chart 44. The instrument 10 is then reversed again, allowing the dentist to resume examining the patient, and the cycle is repeated until the examination is complete.

When the entire examination is completed and all the necessary information is recorded, the dentist will then prepare the pen-probe 10 for sterilization. To accomplish this, the dentist simply unscrews the plug 20 from cavity 28, reverses the pen portion 13, and threads the sleeve 22 into the cavity 28. It is important to secure the beveled shoulder 32 of the threaded sleeve 22 tightly against the beveled entrance 34 of the threaded cavity 28, as shown in FIG. 5, for sealing purposes. The pen-probe 10 is then in its sterilization configuration, FIGS. 1 and 5, which shields the ball-point pen point 23 from the steam of the autoclave environment. With the pen point 23 securely enclosed in the threaded cavity 28, the dentist may then place the entire pen-probe 10 in the autoclave to sterilize it, and may later reuse the instrument. When using the alternative embodiment of the invention (FIG. 9) the overcap 46 is unscrewed from the instrument 10, thus exposing the ball-point pen point 23. The pen-probe is then used by the dentist to examine the patient, collect information, and record the information collected just as described above. Once an examination is complete, then the pen-probe 10 must be prepared for sterilization. To accomplish this, the dentist takes the overcap 46 and tightly screws it down, as illustrated by arrow 52, onto the instrument 10, thus securing the cap in place. Because the overcap 46 has internal threads 48 which mate with the threaded sleeve 22 of the pen cartridge 15, and because the two Conically beveled surfaces 32, 50 also match up, the pen point 23 is completely sealed off from the steam and pressure of the autoclave. With the overcap 46 secured in place, the instrument 10 is ready for sterilization in the autoclave, so that it can thereafter be reused in future examinations.

It will now be appreciated that the invention provides a periodontal pen-probe which permits dental personnel both to examine patients and record information accurately and efficiently with a single instrument which is nevertheless able to withstand sterilization procedures.

While the principles of the invention have been described above in connection with a specific embodiment, this description is intended only by way of example and not as a limitation on the scope of the invention which is stated more broadly in the appended claims.

The invention claimed is:

1. A sterilizable dental instrument comprising a handpiece, a dental instrument at one end of said handpiece, and a sterilable writing means at the other end of said handpiece, wherein said handpiece is constructed from an autoclavable material and has means including a cavity at said other end for receiving and sealing said writing means within said cavity during autoclaving of said instrument.

2. The instrument of claim 1, wherein said sealing means comprises a threaded connection between said cavity and said writing means.

3. The instrument of claim 1, wherein said writing means comprises a pen constructed to withstand autoclaving temperature and pressure.

4. The instrument of claim 3, wherein said pen comprises a writing point and a reservoir connected to said writing point and containing ink capable of withstanding autoclaving temperature.

5. The instrument of claim 4, further comprising means for reversibly mounting said writing means in said cavity with said writing point either protruding from, or sealed within, said cavity.

6. The instrument of claim 1, wherein said sealing means comprises a removable and replaceable overcap adapted to mate with said other end for covering and sealing said writing means within said overcap during autoclaving, of said instrument.

7. The instrument of claim 6, further comprising a threaded connection between said overcap and said handpiece for sealing and protecting said writing means during sterilization.

* * * * *

UNITED STATES PATENT AND TRADEMARK OFFICE
CERTIFICATE OF CORRECTION

PATENT NO. : 5,161,971

DATED     : November 10, 1992

INVENTOR(S) : Neiner, et al.

It is certified that error appears in the above-identified patent and that said Letters Patent is hereby corrected as shown below:

Col. 1, line 7, please insert a period after "diagnosis".

Col. 3, line 23, please change "o" to --or--.

Col. 4, line 31, please change "28" to --20--;

Col. 4, line 38 after "and" please insert --5)--.

Col. 6, line 19, please change "Coni-" to --coni---;

Col. 6 line 63, please delete the comma after "autoclaving".

Signed and Sealed this

Twelfth Day of October, 1993

Attest:

BRUCE LEHMAN

Attesting Officer

Commissioner of Patents and Trademarks